United States Patent [19]

Irving et al.

[11] Patent Number: 4,529,809

[45] Date of Patent: Jul. 16, 1985

[54] METHOD FOR PRODUCTION OF ARYL SUBSTITUTED ESTERS

[75] Inventors: William H. Irving, Rexford; Arnold Factor, Scotia, both of N.Y.

[73] Assignee: General Electric Company, Schenectady, N.Y.

[21] Appl. No.: 527,584

[22] Filed: Aug. 29, 1983

[51] Int. Cl.$^3$ .............................................. C07C 69/76
[52] U.S. Cl. ................................... 560/075; 562/478
[58] Field of Search .......................................... 560/75

[56] References Cited

U.S. PATENT DOCUMENTS

| | | | |
|---|---|---|---|
| Re. 27,004 | 12/1970 | Meier et al. | 260/473 |
| 3,281,455 | 10/1966 | Steinberg | 260/473 |
| 3,535,368 | 10/1970 | Steinberg | 260/470 |
| 3,954,839 | 5/1976 | Dexter | 560/67 |
| 3,984,460 | 10/1976 | Spivak | 560/75 |

FOREIGN PATENT DOCUMENTS

| | | | |
|---|---|---|---|
| 6012341 | 2/1981 | Japan | 560/61 |
| 6135443 | 10/1981 | Japan | 560/61 |
| 6161350 | 12/1981 | Japan | 560/75 |

*Primary Examiner*—Paul J. Killos
*Attorney, Agent, or Firm*—Richard J. Traverso; James C. Davis; James Magee, Jr.

[57] ABSTRACT

A method for producing high yields of aryl substituted esters of the formula

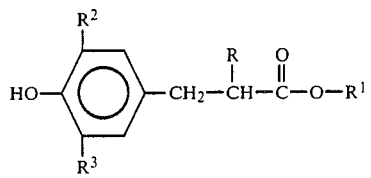

by reacting sterically hindered phenols with a stoichiometric excess of an olefinic ester in the presence of a base catalyst at a temperature in the range of 150° to 250° C.

10 Claims, No Drawings

METHOD FOR PRODUCTION OF ARYL SUBSTITUTED ESTERS

The present invention relates to a method of producing high yields of aryl substituted esters having the formula

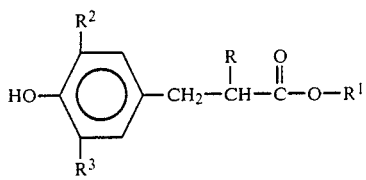

Included among the aryl substituted esters defined by formula I is methyl-2-methyl-3-(3',5'-di-t-butyl-4'-hydroxyphenyl) proprionate herein identified as α-methyl proprionate, which is a key intermediate in the preparation of antioxidants used in polypropylene resins. Pentaerythritol tetrakis [2-methyl-3-(3',5'-di-t-butyl-4'-hydroxyphenyl) proprionate] is an example of such an antioxidant.

The synthesis of such antioxidants have been disclosed by Meier in U.S. Pat. No. RE-27,004, wherein intermediates similar to those of formula I are produced by reaching a 2,6-disubstituted phenol with olefinic esters in the presence of a base catalyst and a solvent. Meier teaches the use of equimolar amounts of reactants and reaction temperatures ranging from 25° to 200° C. The process disclosed by Meier has been found to provide poor yields of the aryl substituted esters of formula I, i.e., where the α-carbon atom is substituted with an alkyl radical, such as α-methyl proprionate. This invention provides an improved process wherein high yields of aryl substituted esters of formula I are obtained, including α-methyl proprionate.

STATEMENT OF THE INVENTION

A method of producing high yields of aryl substituted esters of formula I is provided by reacting a sterically hindered phenol of the formula

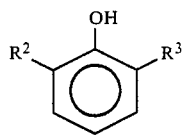

with a stoichiometric excess of an olefinic ester of the formula

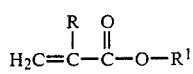

wherein R is a monovalent organic radical selected from a group consisting of alkyl radicals of from 1 to 6 carbon atoms and aryl radicals of from 6 to 15 carbon atoms and $R^1$ is a monovalent organic radical selected from a group consisting of alkyl radicals of from 1 to 20 carbon radicals and aryl radicals of 6 to 20 carbon atoms, in the presence of a catalytic quantity of base at a temperature in the range of about 150°–250° C. under pressure.

Monovalent organic radicals within the scope of R include, for example, methyl, ethyl, n-propyl, isopropyl, butyl, phenyl, xylyl, tolyl, etc.

Monovalent organic radicals within the scope of $R^1$ include, for example, methyl, ethyl, n-propyl, butyl, isopropyl, pentyl, hexyl, heptyl, octyl, amyl, phenyl, xylyl, tolyl, etc.

The monovalent organic radicals which appear on the sterically hindered phenol of formula II, $R^2$ and $R^3$, are selected from the group consisting of secondary and tertiary alkyl groups, of 4 to 24 carbon atoms, such as butyl, amyl, hexyl, heptyl, octyl, nonyl, decyl, t-butyl, isopropyl, etc. The monovalent radicals within the scope of $R^3$ also include alkyl radicals of from 1 to 10 carbon atoms, such as methyl, ethyl, propyl, etc. The preferred monovalent radical for $R^2$ and $R^3$ is the tertiary alkyl group, t-butyl.

Examples of the sterically hindered phenols include 2,6-di-t-butylphenol, 6-(1,1,3,3-tertramethyl-n-butyl)-o-cresol, 6-t-butyl-o-cresol, 2-butyl-6-t-butyl phenol, 2,6-bis(1,1-dimethyl-n-propyl)phenol, 2,6-bis (1-methyl-n-nonyl)phenol, etc. These compounds can either by obtained commercially or can be prepared by known methods of alkylating phenol.

The olefinic esters of formula III more particularly include, methyl methacrylate, ethyl methacrylate, phenyl methacrylate, methyl ethacrylate, methyl n-propyl-acrylate, methyl isopropyl-acrylate, methyl butyl-acrylate, methyl phenyl-acrylate, etc. The preferred olefinic ester is methyl methacrylate. Compounds of formula III are available commercially in some cases and where they are not available, they may be prepared by esterification of the corresponding acrylic acid derivative. For example, methyl methacrylate is made by esterification of methyacrylic acid with methanol.

Aryl substituted esters which may be produced by this invention more particularly include:
methyl-2-methyl-3-(3',5'-di-t-butyl-4'-hydroxy phenyl)-proprionate
ethyl-2-methyl-3-(3',5'-di-t-butyl-4'-hydroxy phenyl) proprionate
propyl-2-methyl-3-(3',5'-di-t-butyl-4'-hydroxy phenyl) proprionate
methyl-2-ethyl-3-(3',5'-di-t-butyl-4'-hydroxy phenyl) proprionate
methyl-2-propyl-3-(3',5'-di-t-butyl-4'-hydroxy phenyl)-proprionate
ethyl-2-ethyl-3-(3',5'-di-t-butyl-4'-hydroxy phenyl)-proprionate
methyl-2-butyl-3-(3',5'-di-t-butyl-4'-hydroxy phenyl) proprionate
and methyl-2-phenyl-3-(3',5'-di-t-butyl-4'-hydroxy phenyl)proprionate.

The reaction is conducted with a stoichiometric excess of the olefinic ester. Molar ratios of olefinic ester to sterically hindered phenol providing a value within the range of 1.5–5.0 are preferred. The percent yield of these aryl substituted esters increases as the quantity of olefinic ester increases. A molar ratio of olefinic ester to sterically hindered phenol providing a value of 3 is most preferable.

The reaction will proceed over a wide range of temperatures from about 25° C. to about 250° C. However, the yields of aryl substituted ester, such as α-methyl proprionate, are low at low temperatures. It is preferable to utilize a reaction temperature above 150° C., which requires the reaction mixture be maintained under pressure. The preferred temperature range is from about 150° to 220° C.

Suitable base catalysts include quaternary ammonium base, such as benzyl trimethyl ammonium methoxide; alkali metal amides, such as sodamide; alkali metal alkoxides, such as sodium and potassium methoxide, ethoxide, n-propoxide, isopropoxide, n-butoxide, s-butoxide, t-butoxide, pentoxide. The alkaline earth metal alkoxides are also suitable.

Any suitable base catalyst concentration may be employed. For example, suitable mole ratios of base to sterically hindered phenol provide values ranging from about 0.01 to about 1.0. The preferred concentration of base catalyst falls in the range of 5–25 mole percent based on the sterically hindered phenol concentration.

The reaction can take place in the presence of a solvent. Suitable solvents include alcohols, such as ethanol, methanol, propanol, t-butanol, t-pentanol, t-hexanol, t-octanol, isopropanol, etc. Any concentration of solvent is suitable for the reaction to occur, however, the preferred amount of solvent is that which provides a concentration of reagents within the range of about 5 to about 30 weight percent.

Where the reaction proceeds in the preferred temperature ranges, the reaction mixture must be maintained under pressure due to the low vapor pressure of the reactants. Suitable pressures range from about 50 psi to 900 psi. Any pressure which maintains the reactants in solution is suitable. The actual pressure is dependent on the temperature and solvent utilized.

The following examples illustrate this invention and are not intended to limit the scope of this invention to their contents.

EXAMPLE I

All reagents were assembled in a glass tube under a dry nitrogen inert atmosphere. The glass tube contained 5.2 milliliters of a 1 mole percent t-butoxide/t-butanol solution, 0.8 grams of 2,6-di-t-butyl phenol and 1.2 grams of methyl methacrylate. The glass tube was immersed in a liquid nitrogen bath (to immobilize reagents in a solid matrix), evacuated under reduced pressure (to deoxygenate the reaction environment) and then sealed. The sealed tube was heated to 155° C. for 23 hours. The alcohol solvents were removed from the reaction mixture with a rotary evaporator and the mixture was acidified with 2 milliliters of 0.1 N HCl. The acidified mixture was diluted with 15 milliliters of toluene and then extracted twice with 2 milliliters each of distilled water. The isolated toluene layer was evaporated under reduced pressure to obtain 1.18 grams of a viscous yellow oil. Gas phase chromatographic (G.P.C.) analysis indicated a 99% yield of α-methyl proprionate.

EXAMPLES II–V

In examples II–V a 300 milliliter stainless steel high pressure reactor equipped with a mechanical stirrer, heating coils, a thermocouple to monitor the internal reaction temperature and a pressure gauge was utilized. In each of the Examples II–V, 22.54 grams of 2,6-di-t-butyl phenol with 140 milliliters of 1.0 mole percent potassium t-butoxide/t-butanol solution were added in the stainless steel pressure reactor. This was followed by rapid addition of methyl methacrylate. The quantity of methyl methacrylate added was 16.44 grams, 32.87 grams, 43.83 grams, and 54.78 grams for each of the Examples II–V, respectively. The reaction system was thoroughly purged with dry nitrogen gas and sealed under the dry nitrogen atmosphere. The closed system was vigorously stirred and heated to 155° C. for 15 hours. The results for each of the following examples are illustrated in Table I.

TABLE I

| Exp. # | MMA/DBP[a] | Tem. (°C.) | Time (Hrs.) | Rel. % Prod. G.P.C. Yield[b] |
|---|---|---|---|---|
| II | 1.5 | 155 | 15 | 18 |
| III | 3.0 | 155 | 15 | 70 |
| IV | 4.0 | 155 | 15 | 77 |
| V | 5.0 | 155 | 15 | 82 |

[a]Molar ratio of methyl methacrylate to 2,6-di-t-butyl phenol
[b]Yield determined by Gas Phase Chromatography

EXAMPLEs VI–IX

The following examples were performed under the same conditions and within the same apparatus as those of examples II–V. However, the reaction temperature was maintained at 215° C. and the reaction time varied from 11 hours to 21 hours. The results obtained are illustrated in Table II.

EXAMPLES X AND XI

These examples demonstrate the results obtained from the process disclosed by Meier. To the same apparatus utilized in examples I–IX, 32.84 grams of 2,6-di-t-butyl phenol, 140 milliliters of a 1.0 mole percent potassium-t-butoxide/t-butanol solution and 32.87 grams of methyl methacrylate were added and treated under a nitrogen atmosphere and sealed. The reaction was vigorously stirred in each of these examples. The reaction temperature was maintained at 25° C. and 55° C. in each of the Examples X and XI, respectively, for 24 hours. The results of these examples are illustrated in Table II below.

TABLE II

| Exp. # | MMA/DBP[a] | Tem. (°C.) | Time (Hrs.) | Rel. % Prod. G.P.C. Yield[b] |
|---|---|---|---|---|
| VI | 1.5 | 215 | 21 | 34 |
| VII | 3.0 | 215 | 18 | 90 |
| VIII | 4.0 | 215 | 11 | 52 |
| IX | 5.0 | 215 | 11 | 55 |
| X | 1.0 | 25 | 24 | <1 |
| XI | 1.0 | 55 | 24 | 7 |

[a]Molar ratio of methyl methacrylate to 2,6-di-t-butyl phenol
[b]Yields determined by Gas Phase Chromatography

What is claimed is:

1. A method of producing high yields of aryl substituted esters of the general formula:

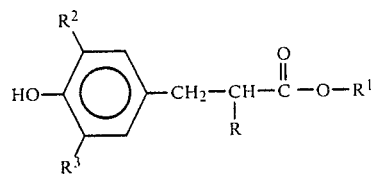

by reacting a sterically hindered phenol of the formula

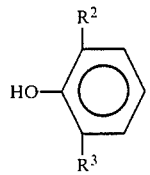

with a stoichiometric excess of an olefinic ester of the formula:

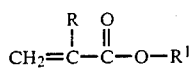

in the presence of a catalytic quantity of base at a temperature in the range of about 150° to about 220° C. under pressure, the molar ratio of said olefinic ester to said sterically hindered phenol having a value above 2, wherein R is a monovalent organic radical selected from the group consisting of alkyl radicals of from 1 to 6 carbon atoms and aryl radicals of from 6 to 15 carbon atoms, $R^1$ is a monovalent organic radical selected from a group consisting of alkyl radicals of from 1 to 20 carbon atoms and aryl radicals of from 6 to 20 carbon atoms, $R^2$ is a monovalent radical selected from the group consisting of secondary and tertiary alkyl groups of from 4 to 24 carbon atoms and $R^3$ is a monovalent organic radical selected from a group consisting of alkyl radicals of from 1 to 10 carbon atoms and secondary and tertiary alkyl radicals of from 4 to 24 carbon atoms.

2. A method as in claim 1 wherein the molar ratio of said olefinic ester and said sterically hindered phenol provides a value in the range of about 2 to about 5.

3. A method as in claim 1 wherein the sterically hindered phenol is 2,6-di-t-butyl phenol.

4. A method as in claim 1 wherein the olefinic ester is a methyl methacrylate.

5. A method as in claim 1 wherein the reaction temperature is maintained at about 215° C.

6. A method as in claim 1 wherein the base is selected from the group consisting of potassium-t-butoxide, sodium methoxide, sodamide and potassium ethoxide.

7. A method as in claim 1 where the reaction takes place within an alcoholic solvent selected from the group consisting of methanol, ethanol, t-butanol, t-pentanol and t-hexanol.

8. A method of producing high yield of

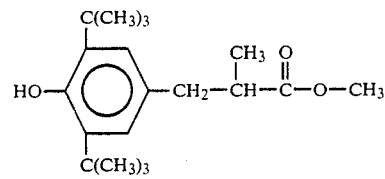

by reacting 2,6-di-t-butyl phenol with an excess of methyl methacrylate which provides a molar ratio of methyl methacrylate to 2,6-di-t-butyl phenol having a value in the range of about 2 to about 5 in the presence of a catalytic quantity of base at a temperature in the range of about 150°-220° C. under pressure.

9. A method as in claim 8 wherein the reaction takes place within a potassium t-butoxide/t-butanol solution.

10. A method as in claim 8 wherein the molar ratio of methyl methacrylate to 2,6-di-t-butyl phenol is about 3 and the reaction temperature is maintained at about 155° C.

* * * * *